United States Patent
Baska (10) Patent No.: US 9,770,567 B2
(45) Date of Patent: Sep. 26, 2017

(54) LARYNGEAL MASK

(75) Inventor: Kanag Baska, Strathfield (AU)

(73) Assignee: Meenakshi Baska, Strathfield, New South Wales (AU)

( * ) Notice: Subject to any disclaimer, the term of this patent is extended or adjusted under 35 U.S.C. 154(b) by 1219 days.

(21) Appl. No.: 13/263,678

(22) PCT Filed: Mar. 25, 2010

(86) PCT No.: PCT/AU2010/000341
§ 371 (c)(1),
(2), (4) Date: Nov. 17, 2011

(87) PCT Pub. No.: WO2010/115232
PCT Pub. Date: Oct. 14, 2010

(65) Prior Publication Data
US 2013/0125897 A1    May 23, 2013

(30) Foreign Application Priority Data

Apr. 8, 2009  (AU) ................................ 2009901521
Apr. 30, 2009  (AU) ................................ 2009901895

(51) Int. Cl.
*A61M 16/04*    (2006.01)

(52) U.S. Cl.
CPC ........ *A61M 16/0434* (2013.01); *A61M 16/04* (2013.01); *A61M 16/0409* (2014.02); *A61M 16/0415* (2014.02); *A61M 16/0418* (2014.02)

(58) Field of Classification Search
CPC .............. A61M 16/04; A61M 16/0409; A61M 16/0418; A61M 16/0434; A61M 25/0105;
(Continued)

(56) References Cited

U.S. PATENT DOCUMENTS

| 4,509,514 A |   | 4/1985 | Brain | 128/207.15 |
| 4,589,410 A | * | 5/1986 | Miller | 128/207.15 |

(Continued)

FOREIGN PATENT DOCUMENTS

| CN | 101057994 A | 10/2007 |
| DE | 298 06 178 U1 | 7/1998 |

(Continued)

OTHER PUBLICATIONS

International Search Report and Written Opinion, PCT/AU2010/000341, mailed Apr. 19, 2010.

(Continued)

*Primary Examiner* — Justine Yu
*Assistant Examiner* — Mark K Han
(74) *Attorney, Agent, or Firm* — Winston & Strawn LLP (57) ABSTRACT

A device for maintaining an airway in a patient, the device including a mask having a peripheral portion that forms a seal with the larynx when the mask is positioned in the laryngo pharynx to thereby prevent ingress of extraneous fluids into the larynx; an airway tube connected to or formed with the mask for passing gas to the larynx when the mask is properly inserted into the laryngo pharynx; and one or more elongated members located on the mask, wherein the application of force to the elongated members causes elastic deformation of the device, thereby facilitating insertion of the device into the patient.

13 Claims, 11 Drawing Sheets (58) Field of Classification Search
CPC .......... A61M 25/0133; A61M 25/0147; A61M 25/0155; A61B 1/0005; A61B 1/0051; A61B 1/0052; A61B 1/267; A61B 1/2673; A61B 1/2676
USPC .......... 128/200.26, 204.18, 206.29, 128/207.14–207.18, 207.29
See application file for complete search history.

(56) References Cited

U.S. PATENT DOCUMENTS

| | | | | |
|---|---|---|---|---|
| 5,529,582 | A | * | 6/1996 | Fukuhara .................. 606/205 |
| 5,682,880 | A | | 11/1997 | Brain .................. 128/207.15 |
| 5,850,832 | A | * | 12/1998 | Chu .................. A61M 16/0409 128/200.26 |
| 6,095,144 | A | | 8/2000 | Pagan |
| 6,321,749 | B1 | * | 11/2001 | Toti et al. .................. 128/207.14 |
| 6,761,170 | B2 | | 7/2004 | Van Landuyt .......... 128/207.14 |
| 2002/0112728 | A1 | | 8/2002 | Landuyt .................. 128/207.15 |
| 2007/0028923 | A1 | * | 2/2007 | Souris et al. .............. 128/207.15 |
| 2008/0236592 | A1 | | 10/2008 | Chen et al. .............. 128/207.15 |
| 2008/0257356 | A1 | * | 10/2008 | Swick .................. 128/207.14 |
| 2012/0090609 | A1 | | 4/2012 | Dubach |

FOREIGN PATENT DOCUMENTS

| | | |
|---|---|---|
| EP | 2 014 326 A1 | 1/2009 |
| EP | 2349425 B1 | 8/2011 |
| GB | 2 111 394 | 7/1983 |
| WO | WO 2005/011784 A1 | 2/2005 |
| WO | WO 2009/026628 A1 | 3/2009 |

OTHER PUBLICATIONS

Supplementary European Search Report, EP10761118, dated Sep. 11, 2014.

* cited by examiner

LARYNGEAL MASK

This application is a 371 filing of International Patent Application PCT/AU2010/000341 filed Mar. 25, 2010.

FIELD OF THE INVENTION

The present invention relates to a device for maintaining an airway in a patient. In preferred embodiments, the present invention relates to a laryngeal mask.

BACKGROUND ART

Maintenance of a viable airway is critical to patient safety during surgical procedures conducted under general anaesthetic. Maintenance of a viable airway during such surgical procedures had, for many years, been achieved by insertion of an endo-tracheal tube into the patient. The endo-tracheal tube was typically inserted through the oral cavity or nasal cavity, into the larynx, through the vocal cords and into the trachea. As the endo-tracheal tube had to be inserted through the vocal cords, difficulty was often experienced in correctly positioning the endo-tracheal tube.

British patent no. 2,111,394 (which corresponds to U.S. Pat. No. 4,509,514) describes a device for maintaining an airway in a patient. The device is described as being an artificial airway device. The device comprises a curved, flexible tube opening at one end into the interior of a hollow mask portion shaped to conform to fit readily into the actual and potential space behind the larynx and to seal around the circumference of the laryngeal inlet without penetrating into the interior of the larynx. Commercial forms of this device have an inflatable collar extending around the periphery of the mask. The inflatable collar is adapted to form the seal around the laryngeal inlet when the collar is inflated. Additionally, the mask portion included an inflatable posterior part which is adapted to press against the back of the throat and thereby increase the sealing pressure around the laryngeal inlet.

British patent no. 2,111,394 states that the shape and (when fitted) the inflatable part or parts of the mask ensure that it approximates closely to the shape of the space between the laryngeal inlet and the walls of the lower part of the throat behind it. Since the walls of tissue forming the back of the throat are relatively rigid, inflation of the mask forces it more tightly against the tissues surrounding the laryngeal inlet, so forming an airtight seal, while tending to anchor the mask in position.

In use of the device described in GB 2,111,394, the device is inserted through the mouth of the patient and down the throat past the epiglottis until the mask comes to rest with its distal end in the base of the throat, lying against the upper end of the normally closed oesophagus. The inflatable ring on the mask is then inflated to seal around the inlet to the larynx. The patient's airway is thus secure and unobstructed and the laryngeal mask can be connected directly to conventional anaesthetic circuit hosing for either positive pressure or spontaneous breathing.

In the device of GB 2,111,394, the mask is associated with an air tube through which air may be passed in order to inflate the inflatable ring, meaning that the device of GB 2,111,394 (the mask and associated air tube) is essentially linear in construction. However, when the device is inserted into a patient, it must follow a curved path as it passes through a patient's mouth and into the throat.

This means that, in order to insert the mask into a patient, a user must manually bend the device to guide it around the curved path into the patient's throat. However, the user must avoid putting his or her fingers into the patient's mouth when inserting the device, meaning that the manual bend placed in the device by the user must be released when the user's fingers come into contact with the patient's teeth. In many cases, such as in cases of patients having long necks, a user will be forced to release the manual bend in the device prior to the device being positioned correctly within the patient's throat. Thus, correctly locating the device in the patient's throat is often difficult and requires additional manipulation.

Some attempts have been made to overcome this problem. For instance, a curved metal introducer may be used in conjunction with the device of GB 2,111,394 that acts in a similar manner to a shoehorn to guide the device into place in the patient's throat. However, both inserting and removing a metal introducer from a patient's throat can be difficult. In addition, inserting a metal device into a patient's mouth and throat has the potential to cause the patient discomfort or injury if the procedure is not carried out correctly.

Other attempts to overcome this problem have included fabricating laryngeal masks having a permanent curve out of rigid or semi-rigid materials. However, the drawback of these devices is that, due to their shape and the material from which they are fabricated, the tip of the device must contact the back of a patient's throat during insertion so that the device may be guided into position. This contact between the device and the patient's throat has the potential to lead to injury to, or discomfort for, the patient.

Thus, there would be an advantage if it were possible to provide a laryngeal mask that was simple and straightforward to correctly insert that minimised the risk of injury or discomfort to the patient.

It will be clearly understood that, if a prior art publication is referred to herein, this reference does not constitute an admission that the publication forms part of the common general knowledge in the art in Australia or in any other country.

Throughout this specification, the term "comprising" and its grammatical equivalents shall be taken to have an inclusive meaning unless the context of use indicates otherwise.

SUMMARY OF THE INVENTION

It is an object of the present invention to provide an improved laryngeal mask which may overcome at least some of the abovementioned disadvantages, or provide a useful or commercial choice.

In order to clearly describe the present invention, the following conventions for determining directions will be used throughout the specification. It will be understood that, when the airway device is positioned properly in a patient, the mask will have a laryngeal side (which is the side closest to the larynx of the patient, which is also referred to as the ventral side or anterior side of the mask) and the other side, being a dorsal side, that is positioned away from the larynx. The distal end of the dorsal side faces towards the oesophagus. The proximal end of the dorsal side faces towards the oropharynx and mouth of the patient. The side of the mask that faces the larynx and when in use will be referred to throughout this specification as the "laryngeal side" or the "ventral side". In terms of directions, throughout the specification, the term "downwards" or its grammatical equivalents will referred to a direction moving towards the laryngeal or ventral side of the mask. Throughout this specification, the term "upwards" or its grammatical equivalents will referred to a direction moving towards the dorsal side of the mask.

In a first aspect, the invention resides broadly in a device for maintaining an airway in a patient, the device comprising:

a mask having a peripheral portion that forms a seal with the larynx when the mask is positioned in the laryngo pharynx to thereby prevent ingress of extraneous fluids into the larynx;

an airway tube connected to or formed with the mask for passing gas to the larynx when the mask is properly inserted into the laryngo pharynx; and deformation means located on the mask, wherein the application of force to the deformation means causes elastic deformation of the device, thereby facilitating insertion of the device into the patient.

The application of force to the deformation means may cause deformation of the mask portion, or deformation of the airway tube or deformation of both the mask portion and the airway tube.

In some embodiments of the invention, the peripheral portion of the mask may include a soft, flexible portion that contacts tissues surrounding the laryngeal opening when the device is inserted into a patient, the soft, flexible portion being arranged whereby application of pressurised gas to the airway tube urges the soft, flexible portion into contact with the tissues surrounding the laryngeal opening or the pharyngeal wall.

In one embodiment, the soft, flexible portion has a part that extends inwardly, the inwardly extending portion being located at a ventral side of the mask. Suitably, the inwardly extending portion includes or defines an opening through which ventilation gases pass. Suitably, the inwardly extending soft, flexible portion is caused to expand when pressurised ventilation gases are applied to the airway. This "inflation" pushes or urges the soft, flexible portion into firmer contact with the tissues surrounding the laryngeal opening with greater force than is present when pressurised ventilation gases are not applied to the airway. As the force with which the soft, flexible portion is pushed into contact with the tissues surrounding the laryngeal opening is increased by pressurised ventilation gases in the airway tube, the seal achieved by the soft, flexible portion with the tissues surrounding the laryngeal opening is also improved. Thus, the strength or effectiveness of the soft, flexible portion in achieving a seal with the tissues surrounding the laryngeal opening is proportional to the pressure of the ventilation gases supplied to the airway tube. This is in direct contrast to existing laryngeal mask airway devices in which the strength of the seal formed with the tissues surrounding the laryngeal opening is dependent upon the inflation pressure of an inflatable cuff (which inflation pressure is independent of the pressure of ventilated gases supplied via the airway tube) or dependent on the strength and resiliency of the material from which the peripheral portion of the laryngeal mask is fabricated. To improve the seal with conventional laryngeal masks, larger sized masks are also frequently used, which can cause increased patient discomfort and longer recovery time. Indeed, in presently available laryngeal masks that include an inflatable cuff to achieve a seal, when the airway pressure is increased during IPPV, the increase in the airway pressure pushes the anterior pharyngeal wall away from the already inflated and fixed peripheral cuff of the mask, which leaves a gap between the mask and the pharyngeal wall. As a result, gas can escape between the fixed inflated cuff and the pharyngeal wall.

In some embodiments, the soft flexible portion lies against and extends along the structures around the larynx when the mask is positioned in the patient, the soft flexible portion being urged or forced into contact with the structures around the larynx when pressurised gas is supplied to the mask.

The soft, flexible portion may comprise a domed membrane, a folded membrane, or a membrane including a portion that extends substantially parallel to the tissues surrounding the laryngeal opening. The soft, flexible portion suitably includes or defines an opening, with the soft, flexible portion desirably having a thin wall thickness in the vicinity of the opening.

In some embodiments, the opening in the soft, flexible portion may include a ring or region of thicker material around or near the opening. This assists in maintaining the shape of the opening.

The soft, flexible portion may be integrally formed with the mask. Alternatively, the soft, flexible portion may be joined to the mask, for example, by use of a suitable adhesive, by ultrasonic welding, or by any other suitable joining technique.

The soft, flexible portion may form part of a larger structure, with the larger structure having portions or regions of thicker wall thickness or less flexibility than the soft, flexible portion. The larger structure may be arranged such that the soft, flexible portion contacts the tissues surrounding the laryngeal opening when the airway device is inserted into a patient. The larger structure may be arranged such that the soft, flexible portion lies against and substantially parallel to the tissues surrounding the laryngeal opening when the airway device is inserted into a patient.

The soft, flexible portion may be utilised with any of the airway devices described in with reference to the other aspects of the present invention, as described herein.

In other embodiments of all aspects of the present invention, the mask may be made from a resilient material. When pressurised ventilation gases are supplied to the airway tube, the increased internal pressure within the mask (arising from the pressurised ventilation gases) will cause the mask to circumferentially expand. The mask may be made of varying wall thicknesses and thus its expansion can vary considerably in different parts of the mask. This expansion tends to increase the seal around the mask in all directions against the pharyngeal walls. As the part of the mask facing the anterior pharyngeal wall (i.e. the tissues surrounding the laryngeal opening) is also made with wall regions of varying thicknesses, the thinner parts expand the most and exert further pressure against the tissues that they are in contact with. This expansion of the mask is caused by the ventilation gases. Thus, the strength or effectiveness of the seal achieved by the mask is proportional to the pressure of the ventilation gases used.

In some embodiments, the device of the present invention may further include one or more loops or brackets attached to or extending from the airway tube to enable the device to be more easily taped or tied in place during use in a patient. In one embodiment, the one or more loops or brackets are positioned on a ventral side of the airway tube. In another embodiment, the one or more loops or brackets are positioned on both a ventral side and a dorsal side of the airway tube.

In yet another embodiment, the airway tube may be provided with one or more depressions to facilitate securing of the mask and for positioning of the fingers of a doctor utilising the device. For example, finger grips for two or more fingers may be formed in the airway tube.

The mask of the present invention may be used for positive pressure ventilation, for resuscitation and for use in anaesthesia.

The deformation means may be of any suitable form and configuration. For instance, the deformation means may be formed integrally with the mask or may be formed separately from the mask and adapted for temporary or permanent attachment thereto using any suitable technique.

In a preferred embodiment of the invention, the deformation means comprises one or more elongate members adapted for attachment to the mask at or adjacent a first end thereof. In some embodiments, the one or more elongate members comprises a flexible member. The deformation means may be fabricated from any suitable material. However, in a preferred embodiment of the invention, the deformation means may be fabricated from the same material as the device. This is particularly the case in embodiments of the invention where the deformation means is formed integrally with the device.

In some embodiments of the invention, the first end of the deformation means may be provided with an attachment portion to assist in attaching the deformation means to the mask. The deformation means may be attached to any suitable part of the mask, including being attached to either the laryngeal or dorsal side of the mask. In embodiments of the invention in which the deformation means is attached to the dorsal side of the mask, the attachment portion may be adapted for attachment to any suitable point on the dorsal side of the mask or to the sides of the mask or on lateral portions of the mask. However, in a preferred embodiment of the invention, the deformation means may be attached to the laryngeal side of the mask. The deformation means may be attached to a distal portion of the mask or to a proximal portion of the mask or even to a mid-portion of the mask.

The attachment portion may be of any suitable form, such as, but not limited to, one or more attachment membranes, elements or the like adapted for attachment to the mask. Preferably, the deformation means is attached to the mask in such a manner that the deformation means lies substantially in line with a longitudinal axis of the device. In an alternative embodiment of the invention, the attachment portion may comprise a substantially Y-shaped member adapted for attachment to the mask.

In other embodiments, the attachment portion may further comprise anchor means adapted to ensure that the deformation means remains in correct alignment when in use. Incorrect alignment of the deformation means could potentially result, for instance, in the deformation means partially or completely blocking the flow of gas to the patient's larynx. The anchor means may be of any suitable form, although in some embodiments of the invention the anchor means may comprise one or more further membranes, elements or the like adapted for connection to both the mask and the attachment portion. In some embodiments of the invention the anchor means may lie substantially along a longitudinal axis of the device. In further embodiments of the invention, the anchor means may be located substantially perpendicular to the attachment portion.

Preferably, the anchor means is attached to at least the attachment portion and the peripheral portion of the mask. However, in other embodiments of the invention, the anchor means may be further adapted for attachment to one or more of the deformation means or the airway tube.

In an alternative embodiment of the invention, the anchor means may not be adapted for attachment to the attachment portion. For instance, the anchor means may be adapted for connection directly to the deformation means. In this embodiment of the invention, the anchor means may be adapted for connection to the deformation means at one end, while at a second end the anchor means may be adapted for connection to the mask, the airway tube, or both. In a preferred embodiment of the invention, the anchor means extends between (and is connected to) the airway tube and the deformation means. This arrangement may be preferred in circumstances in which other anchor means described herein are likely to result in an obstruction in the patient's throat.

When the first end of the deformation means is attached to the mask, applying a force to a second end of the deformation means results in an elastic deformation of the device. Specifically, pulling the second end of the deformation means away from the mask results in an elastic deformation wherein a curve or bend is made in the device, the laryngeal side of the mask being on the inner radius of the curve or bend. A skilled addressee will understand, however, that in alternative embodiments of the invention, it may be desired to elastically deform the mask in such a way that the dorsal side of the mask is on the inner radius of the curve or bend.

In some embodiments of the present invention, the dorsal side may be provided with means adapted to improve the ease with which the device is elastically deformed. Any suitable means may be provided, such as, but not limited to, one or more grooves and/or ribs located on the dorsal side of the mask.

In some embodiments of the invention, the device may be provided with guide means adapted to guide the deformation means when a force is applied thereto. The guide means may be of any suitable form, although in one simple embodiment of the invention, the guide means may be in the form of a loop or arch through which the deformation means is passed and retained. The deformation means may be movable or slidable through the guide means.

In some embodiments of the invention, a plurality of guide means may be provided.

The guide means may be located at any suitable point on the device. However, it is preferred that the guide means is located on an outer surface of the device, preferably on the airway tube. In one embodiment, the guide means may be located on the ventral side of the airway tube.

In embodiments of the invention in which the attachment portion of the deformation means is attached to the dorsal side of the mask, it is preferred that a plurality of guide means are used. For instance, a first guide means may be located on the airway tube (and, preferably, on the ventral side of the airway tube) as described in the previous paragraph, while a second guide means may be located at any suitable location on the mask. Preferably, the second guide means may be provided on the laryngeal side of the mask such that applying a force to the deformation means results in elastic deformation that produces a curve or bend in the laryngeal side of the device. In some embodiments of the invention, the deformation means may comprise a Y-shaped member, meaning that the mask may be provided with a pair of guide means located, for instance, on opposed sides of the mask. Thus, in this embodiment of the invention, three guide means may be present.

In some preferred embodiment of the invention, the device may further comprise retention means adapted to retain the deformation means in place when a force is applied thereto, thereby ensuring that the device remains in its elastically deformed state until such time as the deformation means is released from the retention means. The retention means may be of any suitable form. For instance, the retention means may include one or more adhesive patches, Velcro, a hook and eye arrangement, a loop and tie, a slot or groove into which the deformation means is inserted or the like, or any combination thereof.

In a preferred embodiment of the invention, the retention means may be in the form of a hook adapted to engage with a corresponding slot or eyelet or similar opening in the deformation means.

In some embodiments, the device may be provided with a plurality of retention means.

Prior to insertion of the device into a patient, a force may be applied to the deformation means in order to cause elastic deformation of the device. In embodiments of the invention in which retention means is present, the deformation means may be engaged with the retention means to ensure that the elastic deformation of the device is maintained. If retention means are not present, the deformation means may simply be held by a user so that elastic deformation of the device is maintained manually. In other embodiments of the invention, the deformation means may be retained on or against any other suitable projection located on the airway tube.

Once elastic deformation of the device has been created, the device is inserted into the patient's mouth and manipulated into position in the patient's throat. The elastic deformation of the device means that insertion of the device into the patient's throat is simplified, and there is only a minimal chance of injury or discomfort to the patient.

Alternatively, a force may be applied to the deformation means once the mask has entered the patient's oral cavity.

Once the mask is in position (e.g. the mask forms a seal against the patient's larynx), or at least nearly in position, or indeed once the mask has been inserted past the bend at the back of the patient's throat (the palatopharyngeal curve), the force applied to the deformation means may be released.

In some embodiments, it may be beneficial to release the elastic deformation of the device prior to its positioning against the patient's larynx. Preferably, the elastic deformation of the device is released when the mask is in position to slide down the posterior aspect of the larynx. This allows the dorsal side of the mask to be pushed towards the pharyngeal wall or to enter the piriform recess by means of deviation of the device from the midline. In this way, the device may be prevented from becoming stuck in the patient's larynx.

In another aspect, the invention resides broadly in a method for inserting a laryngeal mask device into a patient, the method comprising the steps of:
 a) elastically deforming the device by applying a force to a deformation means attached to the laryngeal mask;
 b) inserting the laryngeal mask into the patient's mouth and/or oropharynx whilst avoiding the nasopharynx;
 c) ceasing the application of force to the deformation means such that the elastic deformation of the laryngeal mask is released; and
 d) positioning the laryngeal mask against the patient's larynx to form a seal.

In some embodiments of the method of the present invention, step (b) may precede step (a). Desirably, the device is deformed by the deformation means before the device enters the oropharynx. The device may be deformed before it is inserted into the mouth, or it may be deformed within the mouth of the patient. Step (a) may deform a mask portion of the device, or it may deform an airway portion of the device, or it may deform both the mask portion and the airway portion of the device.

It is envisaged that the device of the present invention may include within its scope a number of other features. These features include those described in the applicants' earlier international patent application nos. PCT/AU2004/ 001011 and PCT/AU2008/001259 (published as WO 2009/026628), the entire contents of which are hereby incorporated by reference.

It will also be appreciated that the present invention may be utilised with any deformable laryngeal mask to facilitate insertion of the laryngeal mask. Thus, the present invention is not limited to any specific construction of the laryngeal mask.

BRIEF DESCRIPTION OF THE DRAWINGS

An embodiment of the invention will be described with reference to the following drawings in which.

DETAILED DESCRIPTION OF THE DRAWINGS

It will be appreciated that the drawings have been provided for the purposes of illustrating preferred embodiments of the present invention and that the invention should not be considered to be limited solely to the features as shown in the drawings.

Figure 1:
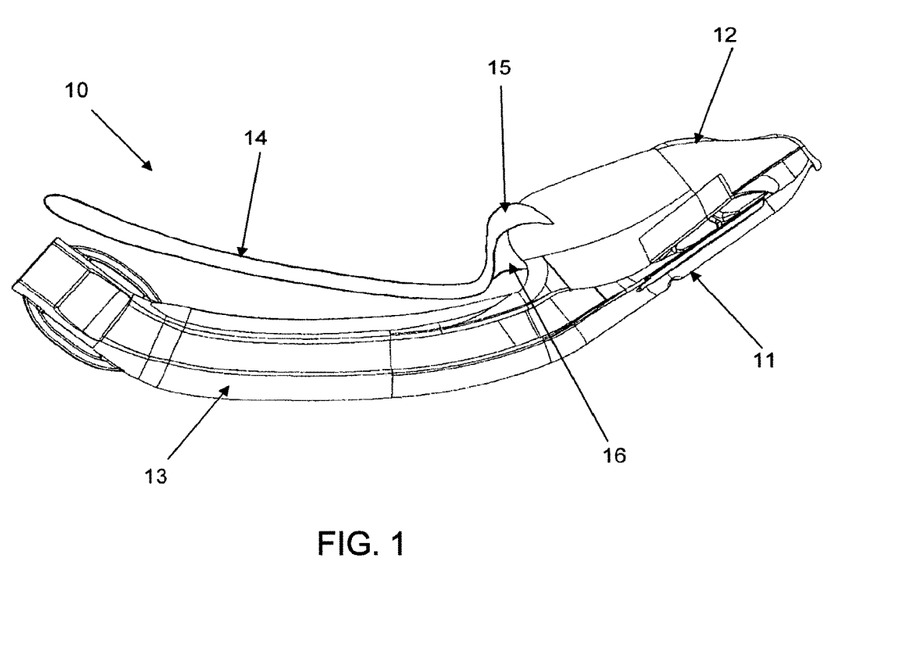
FIG. 1 illustrates a side elevation of a device according to an embodiment of the present invention.

In FIG. 1 there is shown a device 10 according to an embodiment of the present invention. The device 10 comprises a mask 11 having a peripheral portion 12 that forms a seal with a patient's larynx (not shown) and an airway tube 13 for passing gas to the larynx when the mask 11 is properly inserted into a patient's laryngo pharynx.

The device 10 further comprises deformation means 14 in the form of a flexible, elongate member adapted for connection to one end to the peripheral portion 12 of the mask 11.

The deformation means 14 comprises an attachment portion in the form of an attachment membrane 15 adapted for connection to the peripheral portion 12 (more specifically, to a proximal and ventral part of the peripheral portion) of the mask 11. Further, the deformation means 14 comprises anchor means in the form of a further membrane 16 adapted for connection to both the attachment membrane 15 and the peripheral portion 12 of the mask 11. The anchor means 16 is adapted to ensure that the deformation means 14 is retained substantially in line with the air way tube 13 and does not block or restrict, for instance, an opening (obscured) in the peripheral portion 12 through which gas is passed to the patient. This is achieved, in part, by the anchor means extending from the membrane in a dorsal direction and being connected to the peripheral portion of the mask generally along a dorsally extending line.

Figure 2:
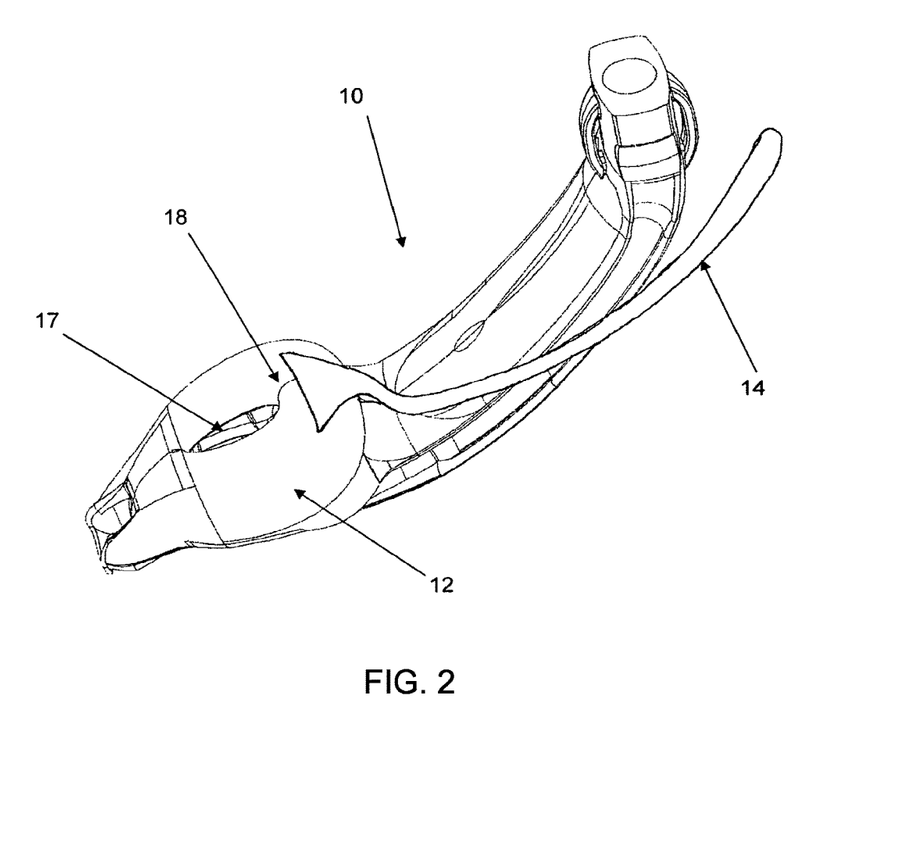
FIG. 2 illustrates a perspective view of a device according to an embodiment of the present invention.

In FIG. 2, a perspective view of the device 10 is shown. In this Figure, it may be more clearly seen that the peripheral portion 12 comprises an opening 17 through which gas is passed to the patient. The anchor means (obscured) is adapted to prevent the deformation means 14 from blocking or restricting the flow of gas through the opening 17.

In this Figure it may be seen that the deformation means 14 is located substantially centrally on a centre line 18 of the device 10. The location of the deformation means 14 substantially along a centre line 18 of the device 10 is preferred so that when a force is applied to the deformation means 14, the mask 11 is elastically deformed uniformly, and no skewing of the mask 11 occurs. Further, the attachment membrane 15 extends laterally on either side of the centre line 18 and is attached to the peripheral part 12 of the mask along a laterally extending line or at least at either end of the laterally extending line. This provides for a more uniform deformation force being applied to the mask.

Figure 16:
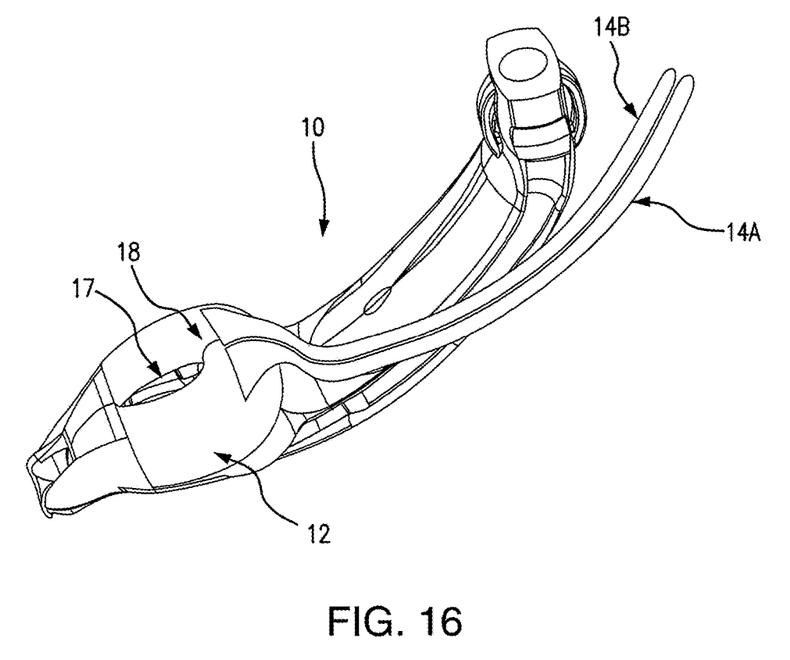
FIG. 16 is a perspective view of a device according to another alternative embodiment of the present invention.

FIG. 16 is a perspective view of an alternative device 10 which is similar to FIG. 2 and uses the same numerals for the same parts. In this Figure, the deformation means is present as two elongated members 14A, 14B located substantially centrally on a centre line 18 of the device 10.

Figure 3:
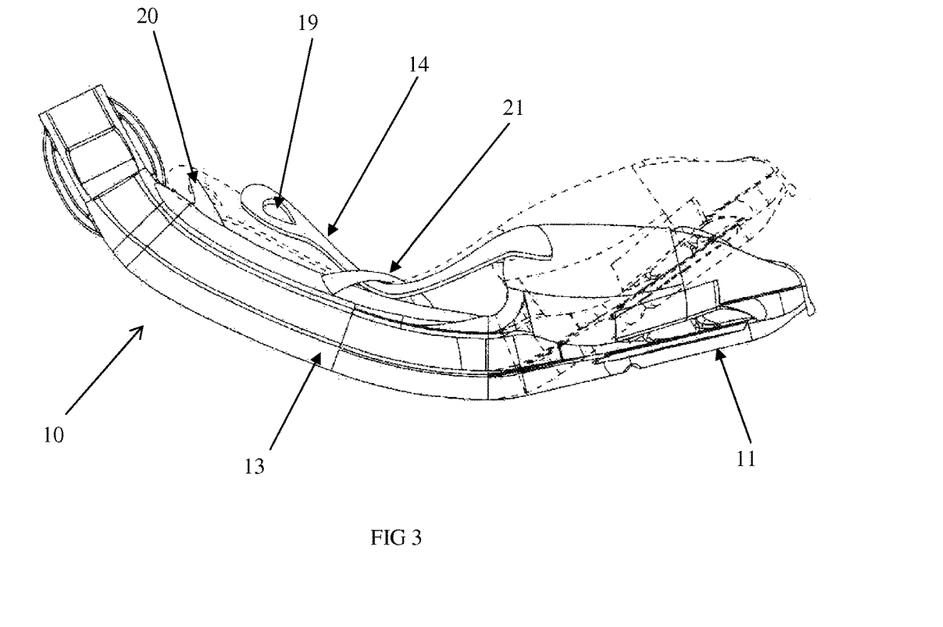
FIG. 3 illustrates a side elevation of a device according to an embodiment of the present invention.

Turning now to FIG. 3 there is shown a side view of a device 10 according to an embodiment of the present invention. In this Figure, the dotted lines represent the device 10 in its elastically deformed state, while the solid lines represent the device 10 when no force is being applied to the deformation means 14. It may be seen that when the device 10 is elastically deformed (shown by the dotted lines) a curve or bend is placed in the device 10 such that the laryngeal side of the mask 11 is on the inner radius of the curve or bend.

To elastically deform the device 10, a force (specifically, a pulling force) is applied to the deformation means 14. The deformation means 14 is provided with an opening 19 in one end adapted to engage with retention means in the form of a hook 20 located on the outer surface of the airway tube 13. When the opening 19 is placed over the hook 20, the device 10 will be retained in its elastically deformed state until such time as the engagement between the deformation means 14 and the hook 20 is released. By providing retention means such as the hook 20, the device can be maintained in the elastically deformed state meaning that a user has two hands free to manipulate the device 10 into position in the patient's throat. Once in position (or at least, close to being in position), the user can release the deformation means 14 from its engagement with the hook 20 so that the device 10 may be correctly installed.

The device 10 shown in FIG. 3 is also provided with guide means 21. In use, the elongate member that forms the deformation means 14 is passed between the guide means 21 and the outer surface of the airway tube 13. In this way, the position of the deformation means 14 may be controlled, both in terms of ensuring that it will come easily to hand when a user requires it, and also in terms of ensuring that, when a force is applied to the deformation means 14, that the deformation means 14 do not come into contact with the patient's teeth or the like. The guide means 21 also assists in ensuring that the deformation means deforms the mask into a desired deformed geometry that facilitates insertion of the mask into the patient.

Figure 4:
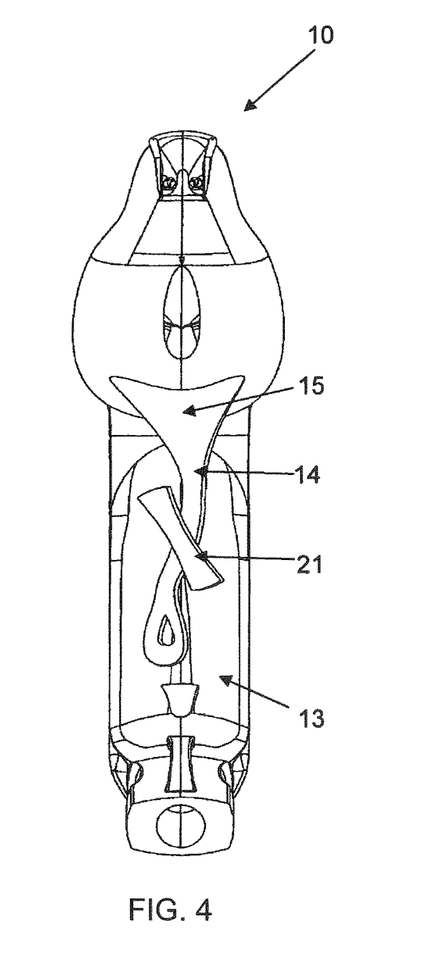
FIG. 4 illustrates a plan view of a device according to an embodiment of the present invention.
Figure 5:
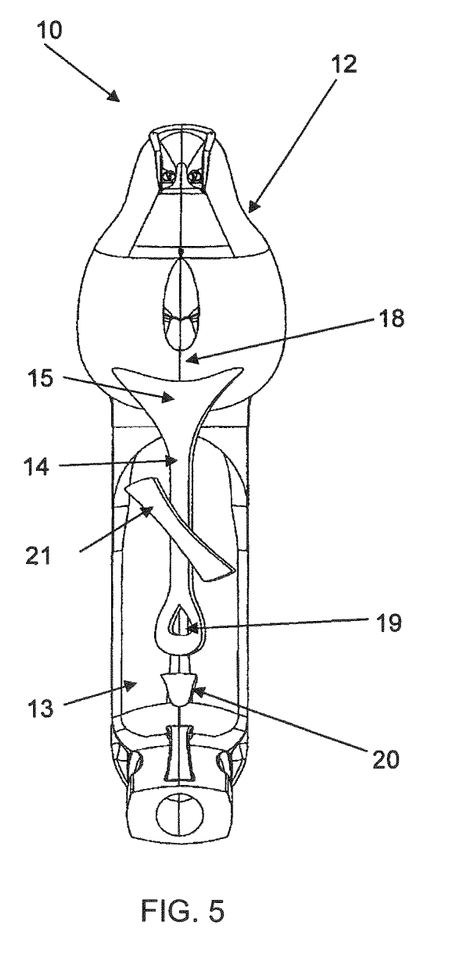
FIG. 5 illustrates a plan view of a device according to an embodiment of the present invention.

In FIGS. 4 and 5, plan views of the laryngeal side of a device 10 according to an embodiment of the present invention are illustrated. In FIG. 4, the device 10 is shown in its non-elastically deformed state, meaning that the deformation means 14 lies loosely against the outer surface of the airway tube 13. The deformation means 14 is passed between the guide means 21 and the outer surface of the airway tube 13, meaning that the deformation means 14 is always readily at hand when required by a user. In addition, the presence of the guide means 21 ensure that, when a pulling force is applied to the deformation means 14 (as shown in FIG. 5), the force is applied substantially along the centerline 18 of the device 10, ensuring that the mask 11 is uniformly elastically deformed.

In these Figures it may also be seen that the attachment membrane 15 of the deformation means 14 is attached to the mask 11 in such a manner that it is located substantially symmetrically about the centerline 18 of the device 10. This also assists in ensuring that the deformation of the mask 11 is substantially uniform.

In FIG. 5, the deformation means 14 may either be held manually by the user applying the force to maintain the device 10 in the elastically deformed state, or the opening 19 in the deformation means 14 may be engaged with the hook 20 located on the laryngeal side of the airway tube 13.

Figure 6:
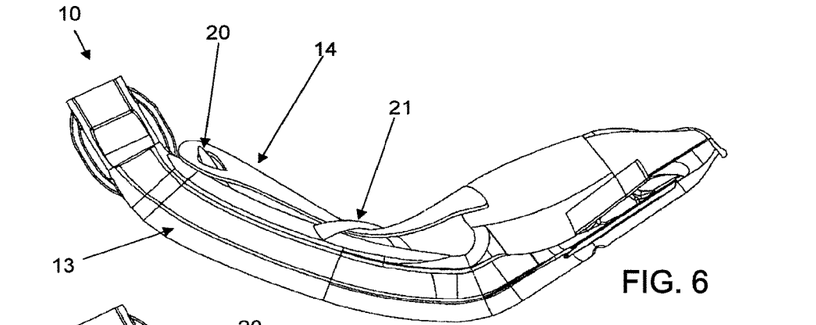
FIGS. 6-8 illustrate side views of a sequence of steps in the use of a device according to an embodiment of the present invention.
Figure 7:
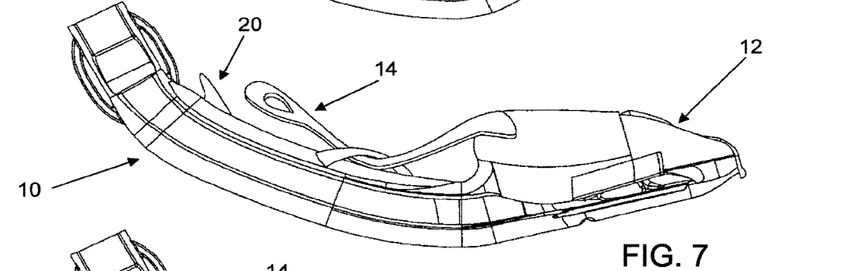
Figure 8:
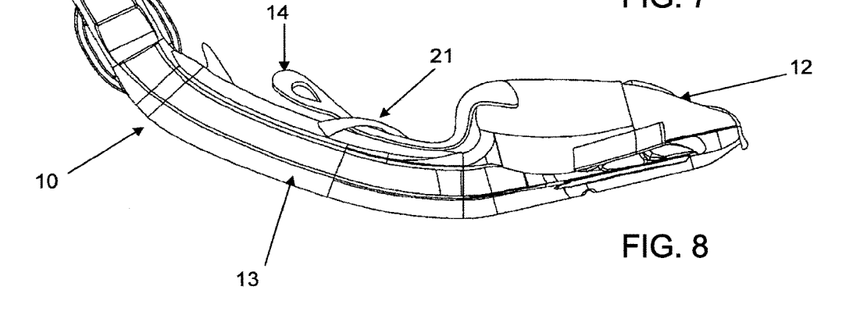

In FIGS. 6 to 8, steps in the use of the device 10 according to an embodiment of the present invention are illustrated. In FIG. 6, the device 10 is shown in its elastically deformed state, and ready for insertion into a patient's throat, in which the deformation means 14 is engaged with a hook 20 and a curve is placed in the device 10 with the laryngeal side of the device 10 being on the inner radius of the curve. In this Figure, the guide means 21 ensure that the deformation means 14 is retained close to the surface of the airway tube 13, meaning that the deformation means 14 will not come into contact with the patient's teeth or the like when being inserted.

In FIG. 7, the device 10 will have been inserted into the patient's throat and will be correctly positioned so that the mask 11 forms a seal with the patient's larynx, or at least close to being correctly positioned. At this point, the deformation means 14 may be released from its engagement with the hook 20, meaning that the device 10 begins to return to its non-elastically deformed state.

In FIG. 8, the device 10 has returned to its non-elastically deformed state. It is envisaged that, when in this state, the device 10 will be correctly positioned such that the mask 11 forms a seal against the patient's larynx.

When no force is being applied to the deformation means 14 (such as in FIG. 8) the guide means 21 still serves to retain the deformation means 14 in position against the outer surface of the airway tube 13. In this way, the deformation means 14 is always maintained close to hand when required, and also the likelihood of the deformation means blocking or restricting an opening (obscured) in the mask 11 through which gas is passed to the patient is reduced.

Figure 9:
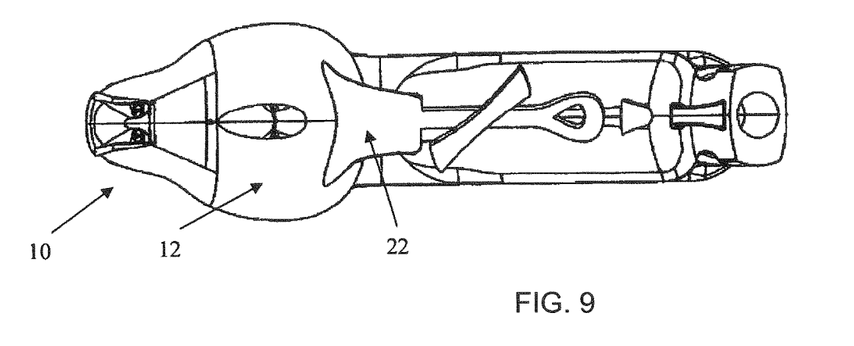
FIGS. 9-10 illustrate plan view of a device according to an alternative embodiment of the present invention.
Figure 10:
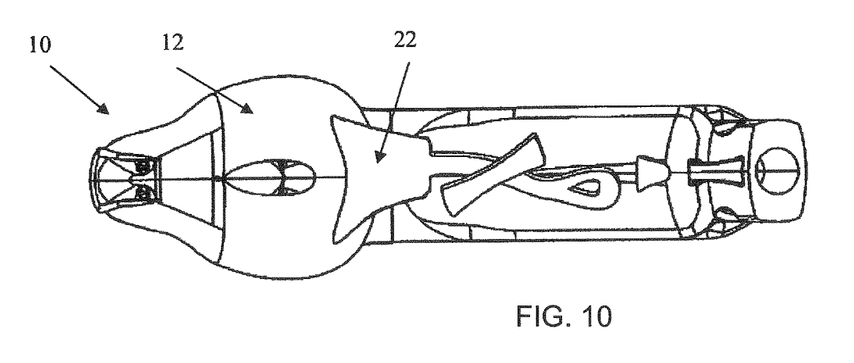

In FIGS. 9 and 10, plan views of a device 10 according to an alternative embodiment of the present invention are illustrated. In this embodiment, the attachment portion 22 is in the form of a large membrane attached to the proximal end of the laryngeal side of the mask 11. An advantage of this enlarged attachment portion 22 is the enlarged attachment portion 22 prevents excessive deformation of the mask 11.

Figure 11:
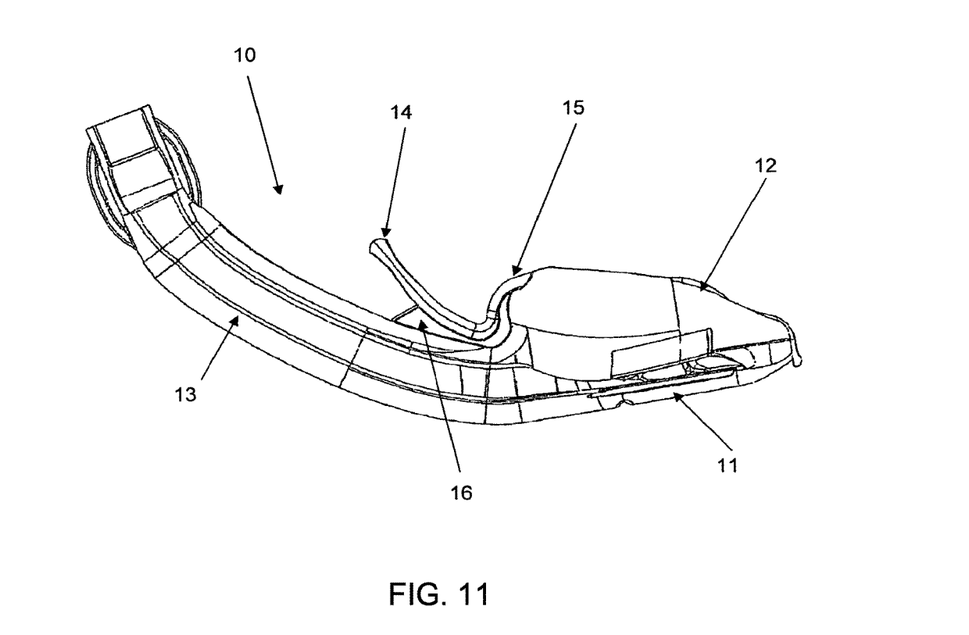
FIG. 11 illustrates a side elevation of a device according to an embodiment of the present invention.

In FIG. 11, a side view of a device 10 according to an alternative embodiment of the invention is shown. The device 10 comprises a mask 11 having a peripheral portion 12 that forms a seal with a patient's larynx (not shown) and an airway tube 13 for passing gas to the larynx when the mask 11 is properly inserted into a patient's laryngo pharynx.

The device 10 further comprises deformation means 14 in the form of a flexible, elongate member adapted for connection to one end to the peripheral portion 12 of the mask 11.

The deformation means 14 comprises an attachment portion in the form of an attachment membrane 15 adapted for connection to the peripheral portion 12 (more specifically, to a proximal and ventral part of the peripheral portion) of the mask 11. Further, the deformation means 14 comprises anchor means in the form of a further membrane 16 adapted for connection to the attachment membrane 15, the peripheral portion 12 of the mask 11, the elongate portion of the deformation means 14 and the airway tube 13. The anchor means 16 is adapted to ensure that the deformation means 14 is retained substantially in line with the air way tube 13 and does not block or restrict, for instance, an opening (obscured) in the peripheral portion 12 through which gas is passed to the patient. This is achieved, in part, by the anchor means extending from the membrane in a dorsal direction and being connected to the peripheral portion of the mask generally along a dorsally extending line.

The advantage of the arrangement illustrated in FIG. 11 is that the anchor means 16 allows the mask 11 and the airway tube 13 to be curved when being inserted into a patient. In addition, the deformation means 14 may be prevented from folding over and blocking or restricting the opening (obscured) in the peripheral portion 12 through which gas is passed to the patient. Finally, the location of the anchor means 16 prevents excessive bending of the device 10.

Figure 12:
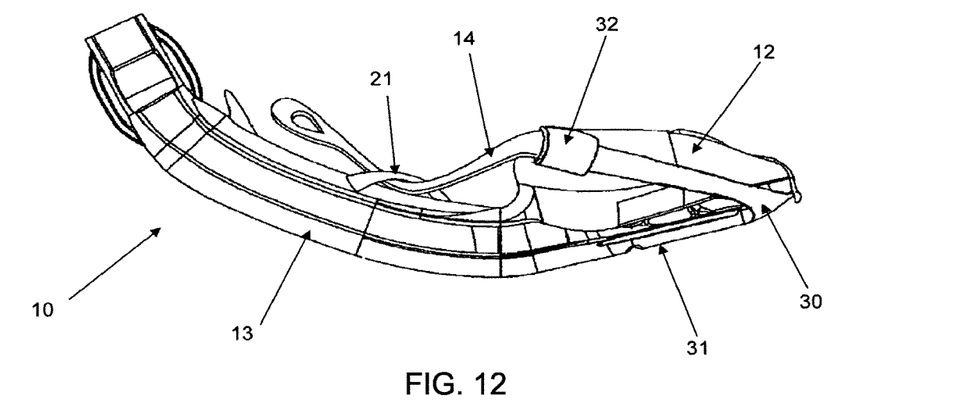
FIG. 12 illustrates a side elevation of a device according to an embodiment of the present invention.

In FIG. 12 there is shown a side elevation of a device 10 according to an embodiment of the present invention. The device 10 shown in FIG. 12 functions in a very similar manner to the device illustrated in FIGS. 6 to 8, with the exception that the attachment portion 30 of the deformation means 14 is adapted for attachment to the dorsal side 31 of the mask 11 at a distal end thereof. In this embodiment of the invention, the device 10 is provided with a first guide means 21 located on the ventral side of the airway tube 13 and a second guide means 32 located on the laryngeal side of the mask 11. In some embodiments of the invention, a third guide means (not shown) may be provided in a corresponding position on the opposite side of the mask 11. In this embodiment of the invention, the deformation means 14 may be in the form of a Y-shaped member.

Figure 13:
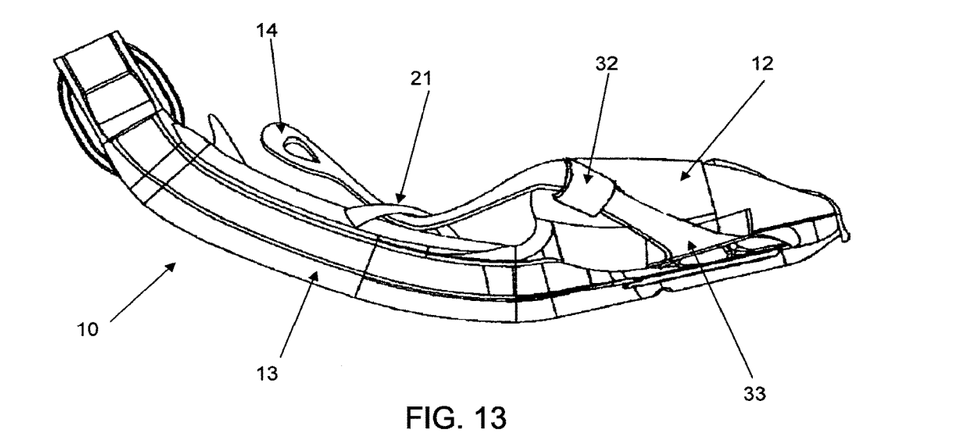
FIG. 13 illustrates a side elevation of a device according to an alternative embodiment of the present invention.

The deformation means passes through both first 21 and second 32 guide means such that applying a force to the deformation means 14 causes an elastic deformation of the device wherein a curve or bend is put into the laryngeal side of the device 10. In FIG. 13, a further embodiment of the invention is shown in which the attachment portion 33 of the deformation means 14 us attached to a side wall of the mask 11. As with the embodiment of the invention shown in FIG. 12, the device 10 of FIG. 13 has a first guide means 21 located on the laryngeal side of the airway tube 13, and a second guide means 32 located on the laryngeal side of the mask. A third guide means (obscured) may be located in a corresponding position on the opposite side of the mask, meaning that the deformation means 14 is a Y-shaped member adapted for connection to opposed side walls of the mask 11.

Figure 14:
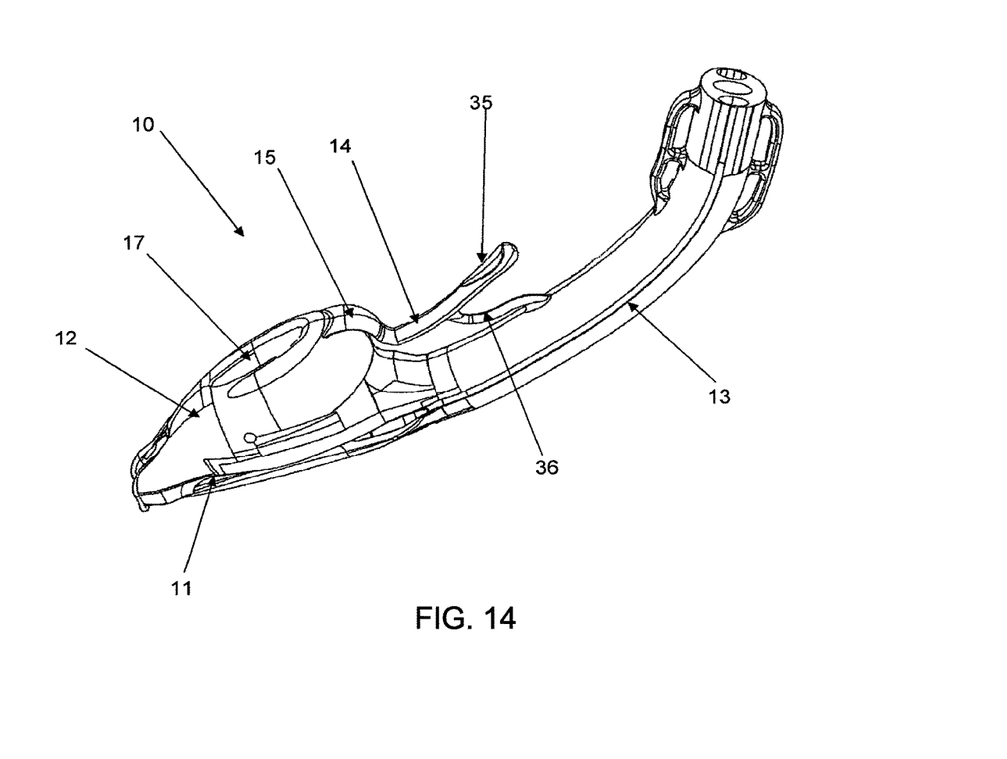
FIG. 14 illustrates a perspective view of a device according to an alternative embodiment of the present invention.

In FIG. 14, a perspective view of a device 10 according to an alternative embodiment of the invention is shown. The device 10 functions in a very similar manner to that shown in FIG. 11. The device 10 comprises a mask 11 having a peripheral portion 12 that forms a seal with a patient's larynx (not shown) and an airway tube 13 for passing gas to the larynx when the mask 11 is properly inserted into a patient's laryngo pharynx.

The device 10 further comprises deformation means 14 in the form of a flexible, elongate member adapted for connection to one end to the peripheral portion 12 of the mask 11. The deformation means 14 comprises a shallow recess or depression 35 at or adjacent one end thereof into which a user's fingertip may be placed during use to improve the user's grip on the deformation means 14.

The deformation means 14 comprises an attachment portion in the form of an attachment membrane 15 adapted for connection to the peripheral portion 12 (more specifically, to a proximal and ventral part of the peripheral portion) of the mask 11. Further, the deformation means 14 comprises anchor means in the form of an elongate member 36 adapted for connection to the deformation means 14 and the airway tube 13. The anchor means 36 is adapted to ensure that the deformation means 14 is retained substantially in line with the air way tube 13 and does not block or restrict, for instance, an opening 17 in the peripheral portion 12 through which gas is passed to the patient. This is achieved, in part, by the anchor means 36 extending from the airway tube 13 at a point generally on a longitudinal axis of the airway tube 13.

The anchor means 36 is provided as a curved member in order to improve the ease with which the deformation means 14 may be manipulated when inserting and removing the device 10 from a patient.

Figure 15:
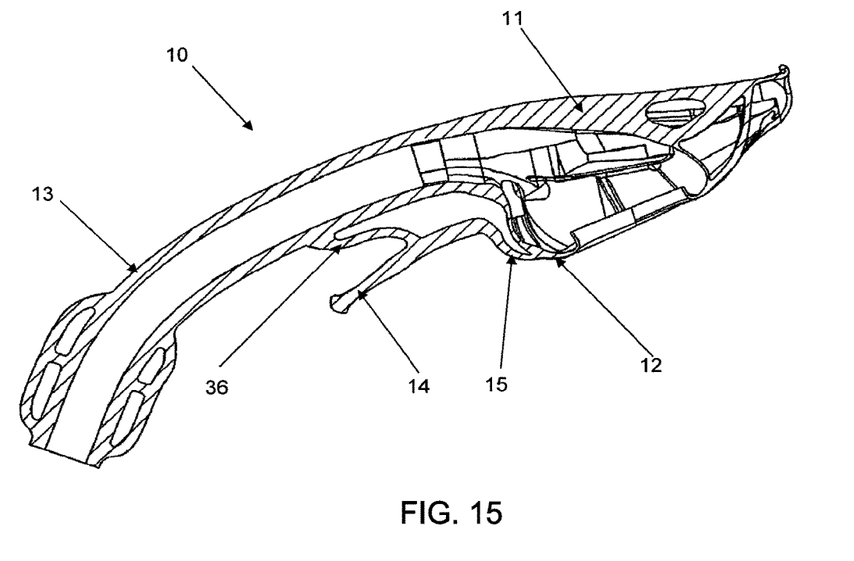
FIG. 15 illustrates a cross-sectional view of a device according to an alternative embodiment of the present invention.

In FIG. 15, a cross-sectional view of the device 10 shown in FIG. 14 is illustrated. It may be more clearly seen in this Figure that the deformation means 14 is connected via the attachment portion 15 to a peripheral portion 12 of the mask 11. The anchor means 36 is attached at a first end to the airway tube 13 and at a second end to the deformation means 14. Providing the anchor means 36 as an elongate member rather than a membrane as illustrated in FIG. 11 reduces the likelihood of the anchor means obstructing the patient's airways or rupturing upon being removed from the patient. In use of the device in accordance with the present invention, the mask portion can be inserted into the oral cavity of the patient and the deformation means used to deform the mask. This facilitates further insertion of the mask into the patient as the tendency for the mask to catch at the back of the patient's throat is significantly reduced. The deformation means can be released once the mask has passed the bend at the back of the patient's throat (the palatopharyngeal curve). This results in the distal end of the airway device extending to a less curved orientation and enables the device to be further inserted and slide down the posterior aspect of the larynx and for the distal tip of the airway device to enter the upper oesophagus as insertion continues. If the curvature caused by tension on the deformation means is maintained until the distal end of the device reaches the larynx, there is a risk that the distal end could get stuck in the larynx. Therefore, it is desirable that tension on the deformation means be released to allow the mask to spring back to its undeformed shape to allow the dorsal part of the mask to be pushed towards the posterior pharyngeal wall or to enter the piriform recess.

Those skilled in the art will appreciate that the present invention may be susceptible to variations and modifications other than those specifically described. It will be understood that the present invention encompasses all such variations and modifications that fall within its spirit and scope.

What is claimed is:

1. A device for maintaining an airway in a patient, the device comprising:
 a mask having a peripheral portion that is adapted to form a seal with the larynx when the mask is positioned in the laryngo pharynx to thereby prevent ingress of extraneous fluids into the larynx;
 an airway tube connected to or formed with the mask for passing gas through an airway opening to the larynx when the mask is properly inserted into the laryngo pharynx; and
 deformation means located substantially centrally on a center line of the device that bisects the peripheral portion and positioned in line with the airway tube, the deformation means comprising at least one elongated member having a first end, an elongated body and an opposed second end, with the first end permanently attached to and integrally formed with the device and unremovably attached in position at a first end thereof to an external surface of the peripheral portion of mask on the laryngeal side of the mask along the center line and at a point proximal to the airway opening,
 wherein an application of force to the opposed second end of the deformation means causes uniform elastic deformation of the airway tube a distal portion of the mask, thereby facilitating insertion of the device into the patient.

2. The device according to claim 1 wherein the first end of the elongated member is provided with an attachment portion to assist in attaching the deformation means to the mask.

3. The device according to claim 2 wherein the attachment portion includes anchor means adapted to ensure that the deformation means remains in line with the airway tube when in use.

4. The device according to claim 3 wherein the anchor means is attached to at least the attachment portion and the peripheral portion of the mask.

5. The device according to claim 1 wherein the first end of the deformation means is located adjacent a proximal portion of the laryngeal side of the mask.

6. The device according to claim 1 wherein pulling the opposed second end of the deformation means of the mask also results in elastic deformation of the airway tube, wherein the elastic deformation includes a curve or bend that is made in the device and airway tube, wherein the laryngeal side of the mask is on the inner radius of the curve or bend.

7. The device according to claim 1 wherein the deformation means is attached to the mask in such a manner that the deformation means lie in line with a longitudinal axis of the device.

8. The device according to claim 1 wherein the device is provided with one or more guide means to guide the deformation means when force is applied to the deformation means.

9. The device according to claim 1 wherein the device further comprises one or more retention means adapted to retain the deformation means in place when force is applied to the deformation means.

10. The device according to claim 9 wherein the retention means is a hook adapted to engage with a corresponding opening in the deformation means.

11. A method for inserting the device of claim 1 into the patient, the method comprising the steps of: a) elastically deforming the airway tube by applying a force to the deformation means attached to the mask; b) inserting the mask into the patient's mouth and/or oropharynx whilst avoiding the nasopharynx; c) ceasing the application of force to the deformation means such that the elastic deformation of the mask is released; and d) positioning the mask against the patient's larynx to form a seal.

12. The method according to claim 11 wherein steps a) and b) of the method are carried out in reverse order.

13. A device for maintaining an airway in a patient, the device comprising:
 a mask having a peripheral portion that is adapted to form a seal with the larynx when the mask is positioned in the laryngo pharynx to thereby prevent ingress of extraneous fluids into the larynx;
 an airway tube connected to or formed with the mask for passing gas through an airway opening to the larynx when the mask is properly inserted into the laryngo pharynx; and
 one or more elongate members located substantially centrally on a center line of the device that bisects the peripheral portion and positioned in line with the airway tube, the elongate member(s) having a first end, an elongated body and an opposed second end, with the first end permanently attached to and integrally formed an external surface of the peripheral portion of mask on the laryngeal side of the mask along the center line and at a point proximal to the airway opening,
 wherein an application of force to the opposed second ends of the one or more elongate members causes uniform elastic deformation comprising a curve or bend of the distal portion of the device and airway tube, with the laryngeal side of the mask being on the inner radius of the curve or bend, thereby facilitating insertion of the device into the patient.

* * * * *